(12) United States Patent
Guarna et al.

(10) Patent No.: US 6,552,034 B2
(45) Date of Patent: Apr. 22, 2003

(54) BENZO[C]QUINOLIZINE DERIVATIVES, THEIR PREPARATION AND USE AS 5α-REDUCTASES INHIBITORS

(75) Inventors: Antonio Guarna, Seano (IT); Mario Serio, Bagno A Ripoli (IT)

(73) Assignee: Applied Research Systems ARS Holding N.V., Curacao (NL)

( * ) Notice: Subject to any disclaimer, the term of this patent is extended or adjusted under 35 U.S.C. 154(b) by 101 days.

(21) Appl. No.: 09/891,088

(22) Filed: Jun. 25, 2001

(65) Prior Publication Data

US 2001/0047098 A1 Nov. 29, 2001

Related U.S. Application Data

(62) Division of application No. 09/117,583, filed as application No. PCT/EP97/00552 on Feb. 7, 1997.

(30) Foreign Application Priority Data

Feb. 9, 1996 (IT) .......................... FI96A0019

(51) Int. Cl.[7] .................. A61K 31/4375; C07D 455/04; C07D 455/06
(52) U.S. Cl. .................. 514/294; 514/294; 546/95; 546/153
(58) Field of Search .................. 514/294; 546/95, 546/153

(56) References Cited

U.S. PATENT DOCUMENTS 3,625,877 A * 12/1971 Jackson ................. 260/24

* cited by examiner

Primary Examiner—Alan L. Rotman
Assistant Examiner—Janet L Coppins
(74) Attorney, Agent, or Firm—Hedman & Costigan P.C.

(57) ABSTRACT

The present invention refers to benzo[c]quinolizine derivatives of general formula (I)

their pharmaceutically acceptable salts or esters, processes for their preparation and pharmaceutical compositions containing them.

11 Claims, 1 Drawing Sheet

BENZO[C]QUINOLIZINE DERIVATIVES, THEIR PREPARATION AND USE AS 5α-REDUCTASES INHIBITORS

The present application is a division of national stage application Ser. No. 09/117,583, filed Jul. 29, 1998, which is a 371 of International Application No. PCT/EP97/00552, filed Feb. 7, 1997 and claims priority to Italian Application Serial No. FI96A000019.

FIELD OF THE INVENTION

The present invention refers to benzo[c]quinolizine derivatives of general formula (I)

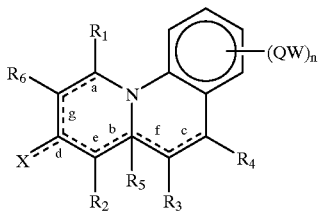

(I)

wherein:

$R_1$, $R_2$, $R_3$, $R_4$, $R_6$, same or different, are chosen in the group consisting of: H, $C_{1-8}$alkyl, $C_{2-8}$alkenyl, $C_{2-8}$alkinyl, cycloalkyl, aryl, heterocycle, halogen, CN, azide, NRR', $C_{1-8}$alkylamino, arylamino, $C_{1-8}$alkyloxy, aryloxy, COOR, CONRR' wherein R and R', same or different, are chosen in the group consisting of: H, $C_{1-8}$alkyl, cycloalkyl, aryl, heterocycle, aryl$C_{1-8}$alkyl;

$R_5$ is chosen in the group consisting of: H, $C_{1-8}$alkyl, COOR, CN, aryl, heterocycle;

X is chosen in the group consisting of: O, C(=O)R, COOR, $NO_2$, CONR'R wherein R and R' are as above defined;

Q is chosen in the group consisting of: simple bond, $C_{1-8}$alkyl, $C_{2-8}$alkenyl, $C_{2-8}$alkinyl, cycloalkyl, CO, CONR, NR, wherein R is as above defined;

W is chosen in the group consisting of: H, $C_{1-8}$alkyl, $C_{2-8}$alkenyl, $C_{2-8}$alkinyl, cycloalkyl, trifluoromethyl, $C_{1-8}$alkoxy, $C_{1-8}$alkoxy-$C_{1-8}$alkyl, aryl$C_{1-8}$alkyl, aryl, aryloxy, arylamino, $C_{1-8}$alkylcarbonyl, arylcarbonyl, halogen, CN, NRR', $C_{1-8}$alkylamino, heterocycle wherein the groups alkyl, alkenyl, alkinyl, cycloalkyl, aryl, heterocycle, can be substitued;

n is an integer comprised between 1 and 4;

the symbol ------ means that the corresponding bonds a, b, c, d e, f, and g can be simple or double bonds;

with the proviso that when b or f are a double bond then the group $R_5$ is absent; and with the proviso that the following two compounds are excluded: 4-carbonitril-2,3-dihydro-(1H)-benzo[c]quinolizin-3-one and 3,4-dihydro-1-phenyl-4aH-benzo[c]quinolizin-3-one;

their pharmaceutically acceptable salts or esters, their process for preparation and their use as inhibitors of steroid 5alpha-reductases (hereinafter indicated as 5alpha-reductases).

The invention refers also to compounds of formula (4)

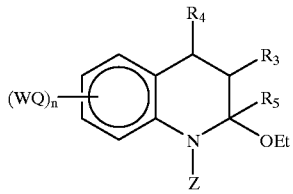

(4)

wherein W, Q, n, $R_3$, $R_4$, $R_5$ are as above defined and Z is a protecting group for the amide-group with the proviso that when $R_3=R_4=R_5=(WQ)_n=H$ than Z is not a group ethoxycarbonyl.

State of the Art

The enzyme known as steroid 5alpha-reductase is a system formed by two iso-enzymes (type I and type II or 5alphaR-I and 5alphaR-II respectively)) which converts testosterone into dihydrotestosterone, the most powerful androgen circulating in the body.

The type I iso-enzyme (5alphaR-I) is mainly present in liver and skin while the type II iso-enzyme (5alphaR-II) is mainly present in the prostate tissue and in the male sexual organs and its activity is essential in the fetal developping process for the differentiation of the external sexual organs.

The production of dihydrotestosterone is associated with some pathologies which are widely diffused as for example benign prostate hypertrophy, prostate cancer, baldness and acne in men and hirsutism in women. More particularly iso-enzyme I plays a role in the pathologies regarding the skin while iso-enzyme-II is involved in prostate pathologies.

In the recent years a lot of international searchers have tried to isolate new compounds capable of inhibiting the 5α-reductase enzyme in order to treat the above said pathologies, especially, if possible, acting selectively on only one of the two iso-enzymes.

Inhibitors of 5α-reductase, and also of the iso-enzymes 5αR-I and 5αR-II were already described, for example finasteride used with success in the treatment of benign prostate hypertrophy [see for example J.Med.Chem. 36, 4313–15 (1993), J.Med.Chem. 37, 3871–74 (1994)]. It is therefore evident the importance of developing new compounds capable of inhibiting the action of the 5α-reductase enzyme and in particular capable of acting selectively on 5αR-I iso-enzyme which, as said, is responsible, of widely diffused pathologies having an high impact as baldness in men and hirsutism in women.

DETAILED DESCRIPTION OF THE INVENTION

The present invention refers to new compounds capable of inhibiting the 5α-reductase enzyme, either selectively in respect of 5αR-I and 5αR-II or on both the iso-enzymes, useful for the treatment of the pathologies mediated by the enzyme.

The products according to the invention have general formula (I)

$$\text{(I)}$$

wherein the substituents $R_1$, $R_2$, $R_3$, $R_4$, $R_5$, $R_6$, X, Q, W, n and the symbol ----- are as above defined.

According to the present invention with group $C_{1-8}$alkyl, $C_{2-8}$alkenyl and $C_{2-8}$alkinyl are indicated linear or branched alkyl radicals as for example: methyl, ethyl, propyl, isopropyl, butyl, pentyl, hexyl, heptyl, octyl, ethylene, propene, butene, isobutene, acetylene, propine, butine ecc.

With cycloalkyl are indicated: cyclopropane, cyclobutane, cyclopentane, cyclohexane, cycloheptane, cyclooctane, norbornane, canphane, adamantane.

With aryl are indicated: phenyl and naphtyl.

Heterocycle means in particular: saturated or aromatic heterocycles containing one or more N atoms, more particularly: piridine, imidazole, pyrrole, indole, triazoles, pyrrolidine, piperidine. Halogen means: fluorine, chlorine, bromine, iodine.

The substituents of the above said group W are preferably: halogen, OR, phenyl, NRR', CN, COOR, CONRR', $C_{1-8}$alkyl (wherein R and R' are as above defined).

In particular, according to the present invention compounds of formula (I) are preferred wherein:

$R_5$=H, heterocycle
X=O
Q=simple bond, CO, CONR, NR (wherein R is as above defined)
W=H, F, Cl, Br, Me, t-butyl, $C_{1-8}$alkoxy, 2,5-dimethylhexyl, trifluoromethyl, 2,5-(di-trifluoromethyl)-phenyl, 4-methoxy-phenyl, 4-fluoro-phenyl, phenyl, phenyl-$C_{1-8}$alkyl, $C_{1-8}$alkylcarbonyl, phenylcarbonyl.
n=1 and 2
$R_1$, $R_2$, $R_3$, $R_4$, $R_6$=H, Me, CN, phenyl, COOR, CONRR' (wherein R and R' are as above defined).

Among the pharmaceutically acceptable esters and salts according to the present invention the following can be mentioned: hydrochloride, sulphate, citrate, formiate, phosphate.

Preferred compounds according to the present invention are:

1,2,4,4a,5,6 hexahydro-(11H)-benzo[c]quinolizine-3-one;
8-chloro-1,2,4,4a,5,6 hexahydro-(11H)-benzo[c]quinolizine-3-one;
1,2,4,4a,5,6 hexahydro-8-methyl-(11H)-benzo[c]quinolizine-3-one;
1,2,4,4a,5,6 hexahydro-8-methyl-(11H)-benzo[c]quinolizine-3-one;
1,2,4,4a,5,6 hexahydro-1-methyl-(11H)-benzo[c]quinolizine-3-one;
1,2,5,6 tetrahydro-(11-H)-benzo[c]quinolizine-3-one;
8-chloro-1,2,5,6 tetrahydro-(11H)-benzo[c]quinolizine-3-one;
8-methyl-1,2,5,6 tetrahydro-(11H)-benzo[c]quinolizine-3-one;
4-methyl-1,2,5,6 tetrahydro-(11H)-benzo[c]quinolizine-3-one;
1-methyl-1,2,5,6 tetrahydro-(11H)-benzo[c]quinolizine-3-one;
4,4a,5,6 tetrahydro-(11H)-benzo[c]quinolizine-3-one;
5,6-dihydro-(11H)-benzo[c]quinolizine-3-one;
8-chloro-4,4a,5,6 tetrahydro-(11H)-benzo[c]quinolizine-3-one;
8-chloro-1-methyl-4,4a,5,6-tetrahydro-(11H)-benzo[c]quinolizine-3-one;
8-methyl-4,4a,5,6 tetrahydro-(11H)-benzo[c]quinolizine-3-one;
4-methyl-4,4a,5,6 tetrahydro-(11H)-benzo[c]quinolizine-3-one (cis) and (trans);
8-chloro-4-methyl-1,2,5,6 tetrahydro-(11H)-benzo[c]quinolizine-3-one;
4,8-dimethyl-1,2,5,6 tetrahydro-(11H)-benzo[c]quinolizine-3-one: 4,8-dimethyl-4,4a,5,6 tetrahydro-(11H)-benzo[c]quinolizine-3-one (cis) and (trans);
8-chloro-4-methyl-4,4a,5,6-tetrahydro-(11H)-benzo[c]quinolizine-3-one (cis) and (trans).

The compounds according to the present invention can be prepared for example starting from compounds of formula 2

$$\text{(2)}$$

wherein $R_3$, $R_4$, W, Q and n are as above defined, following the reaction Scheme reported hereinafter.

The compounds 2 are commercially available or can be prepared according to known techniques.

As it can be seen from the Scheme the preparation of the compounds according to the invention involves the protection of the amide-group in compound 2 by the protecting group Z, for example tert-butoxycarbonyl (t-Boc), to give compound 3; compound 3 is reduced to compound 4, for example (when $R_5$ is H) with sodium borohydride in ethanol (pH 3), which is reacted with a silylether 6, produced "in situ" starting from vinyl-ketones 5 (wherein $R_1$, $R_2$ and $R_6$ are as above defined) with a silylating agent as trimethylsilyltrifluorometansulphonic anhydride (TMSOTf) and thereafter hydrolized, for example in sodium hydrogencarbonate, to give the compounds of formula (I) wherein X=O. The possible introduction of the double bonds and the transformation of the group X in one of the other groups mentioned above can be easily performed according to known techniques starting from the corresponding compound of formula (I) obtained as indicated. For example the introduction of the double bonds in position a or b, can be performed by reaction of dichlorodicyanoquinone (DDQ) with the corresponding silylenolethers or by oxidation with mercuric acetate of the saturated corresponding compound obtained as described above. The transformation of group X can be performed via the corresponding enoltriflates and their carbonylation in the presence of palladium diacetate, triphenylphosphine and the suitable nucleophilic reagent (alcohol, amine, nitro-group).

EXAMPLE 1

Preparation of N-(t-butoxycarbonyl)-3,4-dihydroquinolin-2(1H)-one

[compound 3 wherein (QW)$_n$=H, $R_3$=$R_4$=H]

5 g (34 mmoles) of 3,4-dihydroquinolin-2(1H)-one [compound 2 wherein (QW)$_2$=H, $R_3$=$R_4$=H] and 111 ml of $CH_2Cl_2$ are charged, under nitrogen, in a 250 ml round bottom flask, equipped with magnetic stirrer.

To the above said mixture 4.7 ml (34 mmoles) of triethylamine (distilled on KOH), 8.9 g (40.8 mmoles) of di-butyl dicarbonate and 1 g (8.2 mmoles) of 4-dimethylaminopyridine are added. The mixture is stirred under reflux for 5 h, then for one night at room temperature and thereafter the solvent is removed and 200 ml of water are added. The aqueous phase is extracted with diethylether and the organic phase is neutralized with an aqueous solution of $KHSO_4$ (1 M). The organic phase is washed with a saturated solution of NaCl and dried on $Na_2SO_4$. After filtration and removal of the solvent 8.23 g of the desired product are obtained (white crystals). M.p.: 68–69° C. Yield: 98%.

EXAMPLE 2

Preparation of N-(t-butoxycarbonyl)-2-ethoxy-1,2,3, 4-tetrahydroquinoline [compound 4 wherein $(QW)_n$=H, $R_3$=$R_4$=$R_5$=H].

4.35 g (17.6 mmoles) of the compound obtained from example 1 and 136 ml of absolute ethanol are charged in a 500 ml round bottom flask equipped with magnetic stirrer.

The solution is cooled at −25° C. and 2.66 g (70.4 mmoles) of $NaBH_4$ (subdivided in 6 portions) are added to the mixture in 1 h. After 4 h a solution of HCl 2N in absolute ethanol is added to the mixture, up to pH 3, and the mixture is stirred at 0° C. for 1,5 h. 100 ml of water are added, the aqueous phase is extracted with methylene chloride, the organic phase is washed with a saturated solution of $NaHCO_3$ and a saturated solution of NaCl and the mixture is dried on $Na_2SO_4$. After filtration the solvent is removed and 4,74 g of the expected product are obtained (dense yellow liquid); yield 96%.

Operating as above said other compounds 4 wherein the substituents can not be reduced by $NaBH_4$ are obtained; if substituents which could be reduced by $NaBH_4$ are present these must be previously protected.

EXAMPLE 3

Preparation of 1,2,4,4a,5,6-hexahydro-(11H)-benzo [c]quinolizin-3-one [compound of formula (I) wherein X=O; $(QW)_n$=H; $R_1$=$R_2$=$R_3$=$R_4$=$R_5$=$R_6$=H; a,b,c,e,f,g=simple bond]

70 μl (0.86 mmoles) of 3-buten-2-one [compound of formula 5 wherein $R_1$=$R_2$=$R_6$=H] and 2 ml of anhydrous $CH_2Cl_2$ are charged, at 0° C. under argon in a two-necked round bottom flask equipped with magnetic stirrer and dropping funnel.

170 μl (1.22 mmoles) of triethylamine (distilled on KOH) and 209 μl (1.08 mmoles) of trimethylsilyltrifluorometansulphonate (TMDOTf) (drop by drop) are added to the mixture. In this conditions 2-(trimethylsilyloxy)-1,3-butadiene [compound 6 wherein $R_1$=$R_2$=$R_6$=H] is formed "in situ". The mixture is stirred for 45 minutes and thereafter a solution of 100 mg (0.36 mmoles) of the product from Example 2 in 2 ml of anhydrous $CH_2Cl_2$ is added therein, drop by drop, together with 69 μl (0.36 mmoles) of TMSOTf. The mixture is brought to room temperature and after 30 minutes 4 ml of a saturated solution of $NaHCO_3$ are added and the mixture is stirred vigorously for 36 h.

4 ml of water are added to the mixture and the aqueous phase is extracted with methylene chloride, the organic phase is washed with a saturated solution of $NaHCO_3$, water, a saturated solution of NaCl and is dried on $Na_2SO_4$. After filtration the solvent is removed and 59 mg of crude product are obtained. The product is purified by flash chromatography on silica gel column (FCC) eluting with methylene chloride and triethylamine 1%. 18 mg of the wanted product are obtained (crystals). M.p.: 53–54° C. Yield 25%. Using various vinyl-ketones 5, or using directly the various silylenolethers 6 (when available), it is possible to prepare the corresponding derivatives of formula (I).

In particular when 1-methoxy-3-(trimethylsilyloxy)-1-3-butadiene (compound 6 wherein $R_1$=MeO, $R_2$=H, $R_6$=H) was used, 4,4a,5,6-tetrahydro-(11H)-benzo[c]quinolizin-3-one (compound I wherein X=O, $(QW)_n$=H, $R_1$=$R_2$=$R_3$=$R_4$=$R_5$=$R_6$=H, a=double bond; b,c,e,f,g=single bond] was directly obtained according to the synthesis described in the following Example 4.

EXAMPLE 4

Preparation of 4,4a,5,6-tetrahydro-(11H)-benzo[c] quinolizin-3-one [compound I wherein X=O, $(QW)_n$=H; $R_1$=$R_2$=$R_3$=$R_4$=$R_5$=$R_6$=H; a=double bond; b,c,e,f,g=single bond].

To a stirred solution of compound 4 [$(QW)_n$=H, $R_3$=$R_4$=H] (4 g, 14.42 mmol) of the example 3, in 75 ml of anhydrous $CH_2Cl_2$ under argon at −10° C. is added, dropwise in 7 min, 28.84 ml of a 1M solution of $TiCl_4$ in $CH_2Cl_2$ maintaining the temperature below −5° C. Then 1-methoxy-3-(trimethylsilyloxy)-1-3-butadiene (compound 6, $R_1$=MeO, $R_2$=H, $R_6$=H) (3.29 ml, 17.3 mmol) is added by syringe at 0° C., and the reaction was left aside at room temperature for 1 h. The reaction mixture is added, cautiously, with 100 ml of $NaHCO_3$ saturated solution, and then stirred for 30 min. The organic layer is separated, washed with water, filtered on Celite and dried over $Na_2SO_4$. After removal of the solvent the crude product is purified by flash column chromatography (eluant light-petroleum ether/ethyl acetate 1:4) affording 0.72 g (25% yield) of the expected product (white crystals, m.p.: 135–137° C.).

EXAMPLE 5 a) Preparation of 4-methyl-4,4a,5,6-tetrahydro-(11H)-benzo[c]quinolizine-3-one [compound of formula (I) wherein X=O; $(QW)_n$=H; $R_1$=$R_3$=$R_4$=$R_5$=$R_6$=H; $R_2$=Me; a=double bond; b,c,e,f,g=single bonds], 4 methyl-1,2,5,6-tetrahydro-(11H)-benzo[c] quinolizine-3-one [compound of formula (I) wherein X=O; $(QW)_n$=H; $R_1$=$R_3$=$R_4$=$R_6$=H; $R_2$=Me; b=double bond; a,c,e,f,g=single bonds] and 4-methyl-5,6-dihydro-(11H)-benzo [c]quinolizine-3-one [compound of formula (I) wherein X=O; $(QW)_2$=H; $R_1$=$R_3$=$R_4$=$R_6$=H; $R_2$=Me; a,b=double bonds; c,e,f,g=single bonds]. 1 g (4.64 mmol) of 4-methyl-1,2,4,4a,5,6-hexahydro-(11H)-benzo[c]quinolizine-3-one [compound of formula (I), wherein X=O; $(QW)_n$=H; $R_1$=$R_3$=$R_4$=$R_5$=$R_6$=H; $R_2$=Me; a,b,c,e,f,g=single bonds, obtained according to example 3 by reaction of compound 4 (wherein $(QW)_n$=H; $R_3$=$R_4$=$R_5$=H) of example 2 and ethylvinylketone (compound 5 wherein $R_1$=$R_6$=H; $R_2$=Me] and 120 ml of 5% solution (v/v) of glacial acetic acid in water are charged under nitrogen in a two-necked round bottom flask, equipped with magnetic stirrer, refrigerator and dropping funnel. Under vigorous stirring, 7.27 g (18.56 mmol) of tetrasodic salt EDTA and 5.92 g (18.56 mmol) of $(CH_3CO_2)_2Hg$ are added and the reaction mixture is heated at 90° C. for 2 h. After cooling at room temperature the reaction mixture is added with 120 ml of water and extracted with methylene chloride (4×70 ml). The separated organic phase is washed with a satured solution of $NaHCO_3$, with a satured solution of NaCl then dried over $Na_2SO_4$. After removal of the solvent the crude product is purified by flash chromatography on silica gel by elution with ethylacetate/light petroleum ether 2:1 affording:

83 mg (10%) (gummy solid) of cis-4-methyl-4,4a,5,6-tetrahydro-(11H)-benzo[c]quinolizine-3-one [compound of formula (I) wherein X=O; $(QW)_n$=H; $R_1$=$R_3$=$R_4$=$R_5$=$R_6$=H; $R_2$=Me; a=double bond; b,c,e,f,g=single bonds]

350 mg (40%) (crystals, m.p.: 148–150° C.) of 4 methyl-1,2,5,6-tetrahydro-(11H)-benzo[c]quinolizine-3-one [compound of formula (I) wherein X=O; $(QW)_n$=H; $R_1$=$R_3$=$R_4$=$R_6$=H; $R_2$=Me; b=double bond; a,c,e,f,g=single bonds] and 107 mg (12%) (gummy solid) of 4-methyl-5,6-dihydro-(11H)-benzo[c]quinolizine-3-one [compound of formula (I) wherein X=O; $(QW)_n$=H; $R_1$=$R_3$=$R_4$=$R_6$=H; $R_2$=Me; a,b=double bonds; c,e,f,g=single bonds].

Activity Test

The inhibition potency of the prepared compounds in respect of the iso-enzymes 1 and 2 of 5α-reductase was determined using tissue samples (for example prostate human tissue) or human cellular systems (for example DU 145 cells) expressing iso-enzymes 2 and 1 respectively.

The samples are incubated in the presence of testosterone labelled with tritium and thereafter the quantity of labelled dihydrotestosterone formed in the absence and in the presence of the inhibitor is measured.

The compounds showed high inhibiting power of 5α-reductase enzyme (in particular of iso-enzyme 1) with an inhibition higher than 50% at the concentration of 10–100 nM.

For the therapeutical administration the compounds according to the invention are prepared in the form of pharmaceutical compositions containing the active principle and the organic or inorganic excipients suitable for the oral, parenteral or topic administration of the compositions. The pharmaceutical compositions can thererfore be in the solid form (dragees, suppositories, creams, ointments), liquid form (solutions, suspensions, emulsions) and can possibly contain the stabilizers, conservatives, humectants, emulsifier, buffers or salts used for equilibrating the osmotic pressure which are commonly used in the art.

Generally the administration of the compounds is performed according to the modalities and quantities observed for the known agents used for the same purposes and taking into consideration the age and conditions of the patients.

Figure 1:
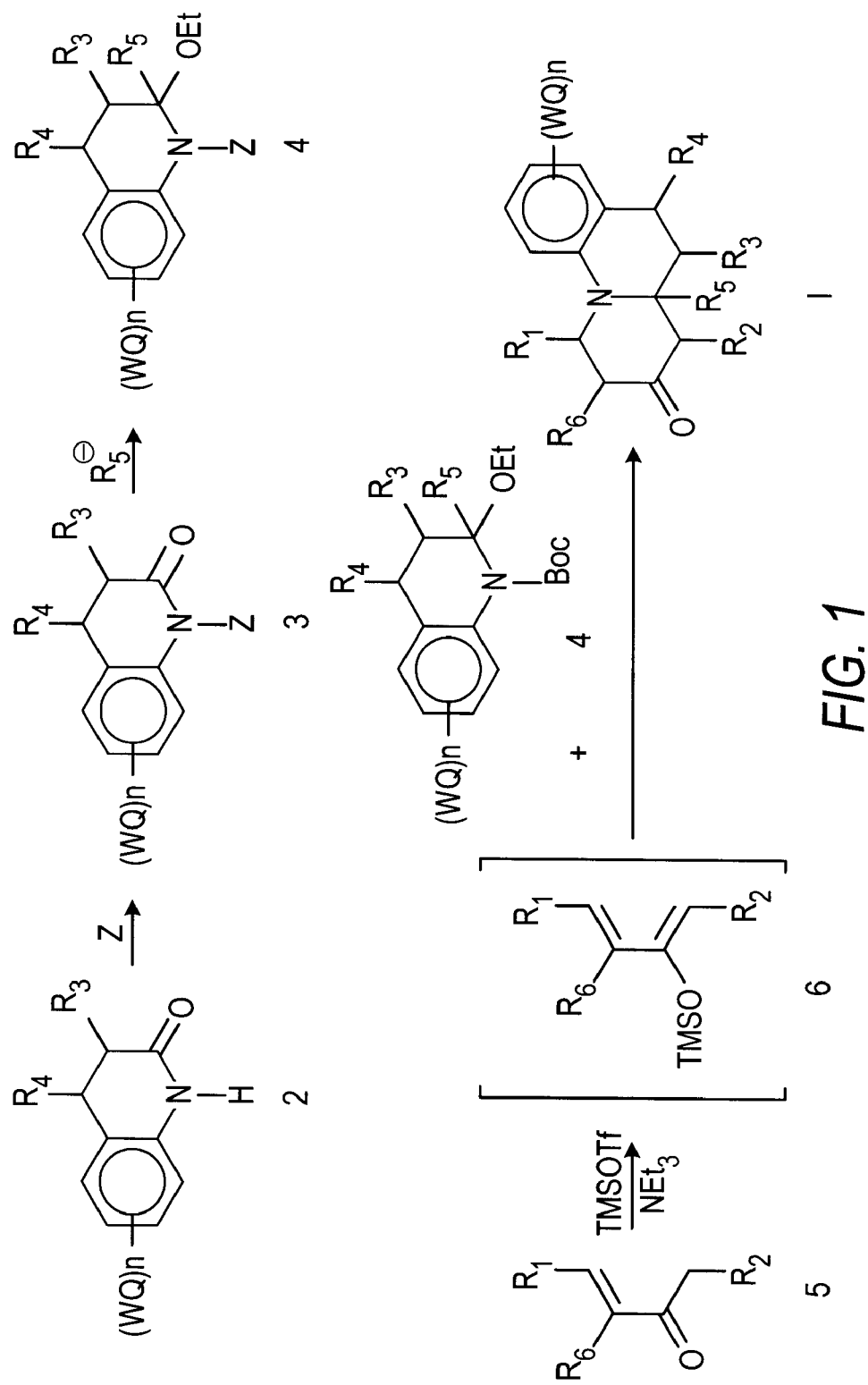
FIG. 1, illustrates a scheme for preparing the compounds of the invention from quinolin-2-one compounds.

What is claimed is:
1. Benzo[c]-quinolizine compounds of formula (I)

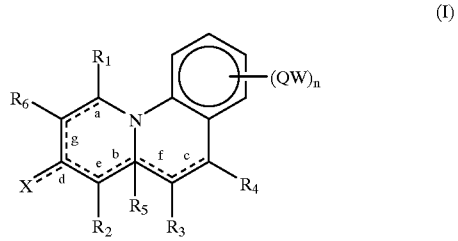

wherein:
$R_1$, $R_2$, $R_3$, $R_4$, $R_6$, same or different, are chosen in the group consisting of: H, $C_{1-8}$alkyl, $C_{2-8}$alkenyl, $C_{2-8}$alkinyl, cyclopropane, cyclobutane, cyclopentane, cyclohexane, cycloheptane, cyclooctane, norbornane, canphane, adamantane, phenyl, naphthyl, saturated or aromatic heterocycle containing one or more N atoms, halogen, CN, azide, NRR', $C_{1-8}$alkylamino, arylamino, $C_{1-8}$alkyloxy, aryloxy, COOR, CONRR' wherein R and R', same or different, are chosen in the group consisting of: H, $C_{1-8}$alkyl, cyclopropane, cyclobutane, cyclopentane, cyclohexane, cycloheptane, cyclooctane, norbornane, canphane, adamantane, phenyl, naphthyl, saturated or aromatic heterocycle containing one or more N atoms, aryl$C_{1-8}$alkyl;

$R_5$ is chosen in the group consisting of: H, $C_{1-8}$alkyl, COOR, CN, phenyl, naphthyl, saturated or aromatic heterocycle containing one or more N atoms;

X is chosen in the group consisting of: O, C(=O)R, COOR, $NO_2$, CONR'R wherein R and R' are as above defined;

Q is chosen in the group consisting of: simple bond, $C_{1-8}$alkyl, $C_{2-8}$alkenyl, $C_{2-8}$alkinyl, cyclopropane, cyclobutane, cyclopentane, cyclohexane, cycloheptane, cyclooctane, norbornane, canphane, adamantane, CO, CONR, NR, wherein R is as above defined;

W is chosen in the group consisting of: H, $C_{1-8}$alkyl, $C_{2-8}$alkenyl, $C_{2-8}$alkinyl, cyclopropane, cyclobutane, cyclopentane, cyclohexane, cycloheptane, cyclooctane, norbornane, canphane, adamantane, trifluoromethyl, $C_{1-8}$alkoxy, $C_{1-8}$alkoxy-$C_{1-8}$alkyl, aryl$C_{1-8}$alkyl, phenyl, naphthyl aryloxy, arylamino, $C_{1-8}$alkylcarbonyl, arylcarbonyl, halogen, CN, NRR', $C_{1-8}$alkylamino, saturated or aromatic heterocycle containing one or more N atoms, wherein the groups alkyl, alkenyl, alkinyl, cyclopropane, cyclobutane, cyclopentane, cyclohexane, cycloheptane, cyclooctane, norbornane, canphane, adamantane, phenyl, naphthyl, saturated or aromatic heterocycle containing one or more N atoms can be substitued by halogen, OR, phenyl, NRR', CN, COOR, CONRR', $C_{1-8}$alkyl (wherein R and R' are as above defined);

n is an integer comprised between 1 and 4;
the symbol ------ means that the corresponding bonds a, b, c, d e, f, and g can be simple or double bonds;
with the proviso that when b or f are a double bond then the group $R_5$ is absent; and with the proviso that the following two compounds are excluded from the claim: 4-carbonitril-2,3-dihydro-(1H)-benzo[c]quinolizin-3-one and 3,4-dihydro-1-phenyl-4aH-benzo[c]quinolizin-3-one;
their pharmaceutically acceptable salts or esters.

2. Process for the preparation of compounds according to claim 1 wherein:

the amide-group of a compound of formula (2)

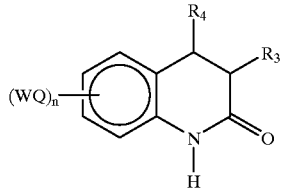

(2)

is protected with a protecting group Z to give the compound (3)

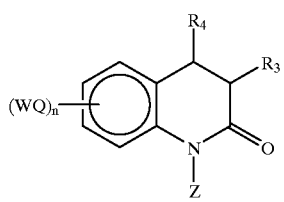

(3)

the above said compound (3) is reduced to compound (4), for example with sodium borohydride in ethanol (pH3)

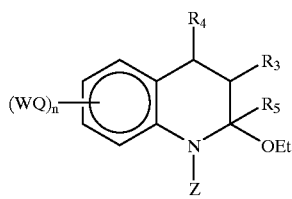

(4)

and compound (4) is reacted with a silylether (6)

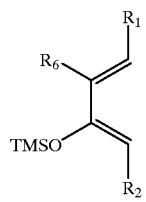

(6)

prepared "in situ" by reacting a vinyl-ketone (5)

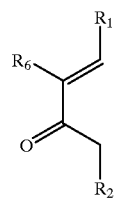

(5)

(wherein $R_1$, $R_2$, $R_6$ are as above defined) with a silylating agent as trimethylsilyltrifluorometan-sulphonic anhydride (TMSOTf) and are finally hydrolized, for example with sodium hydrogencarbonate, to give the final compound of formula (I) wherein X=O.

3. Process according to claim 2 wherein a double bond is introduced in position a or b by reaction of dichlorodicy-anoquinone with the corresponding silylenolether or by oxidation with the mercuric acetate of the satureated compound.

4. Process according to claim 2 wherein X is transformed via the corresponding enoltriflate, carbonylation in the presence of palladium diacetate, triphenylphosphine and a suitable nucleophilic reagent.

5. A pharmaceutical composition which comprises an excipient and a benzo[c]guinolizine compound as defined in claim 1.

6. A method of inhibiting a 5α-reductase enzyme which comprises administering to a host an effective amount of a compound of claim 1.

7. A method of treating acne which comprises administering an effective amount of a compound as defined in claim 1.

8. A method of treating baldness which comprises administering an effective amount of a compound as defined in claim 1.

9. A method of treating prostate cancer which comprises administering an effective amount of a compound as defined in claim 1.

10. A method of treating prostatic hypertrophy which comprises administering an effective amount of a compound as defined in claim 1.

11. A method of treating hirsutism in women which comprises administering an effective amount of a compound as defined in claim 1.

* * * * *